United States Patent [19]

Peyman

[11] Patent Number: 5,743,274
[45] Date of Patent: Apr. 28, 1998

[54] MACULAR BANDAGE FOR USE IN THE TREATMENT OF SUBRETINAL NEOVASCULAR MEMBERS

[76] Inventor: Gholam A. Peyman, 2020 Gravier St., New Orleans, La. 70112-2234

[21] Appl. No.: 617,114

[22] Filed: Mar. 18, 1996

[51] Int. Cl.$^6$ .................. A61B 19/00; A61F 2/14
[52] U.S. Cl. .................. 128/898; 623/4
[58] Field of Search .................. 623/4.5; 602/42, 602/48; 128/898

[56] References Cited

U.S. PATENT DOCUMENTS 4,549,529  10/1985  White .................. 623/4
5,489,299  2/1996  Schachar .................. 623/4

OTHER PUBLICATIONS

Barricks et al. Bare Schera Closure in Retinal Detachment Surgery. Amer. J. of Ophthalmology. pp. 779–781 Dec. 1978.

Scleral Reinforcement by F.B. Thompson, M.D. New York, MacMillan 1990. pp. 267–297.

Santos L., Capeans C., et al. an abstract presented in ARVO, 1994, pp. 1318–1326.

Juancho F C Remulla et al. British Journal of Ophthalmology, Jun. 1995, vol. 79, No. 6, pp. 558–561.

*Primary Examiner*—Robert A. Clarke
*Attorney, Agent, or Firm*—Haverstock, Garrett and Roberts

[57] ABSTRACT

A method of treating a disorder of an eye, the eye having a macular area and a sclera, comprises the step of placing a strip of material over the macular area, the strip having a pair of opposed ends, and suturing the ends to the sclera. A macular bandage is also disclosed which comprises a strip of material having a pair of ends which are sutured to the sclera of the eye after the strip has been placed around the macular area of the eye.

14 Claims, 2 Drawing Sheets

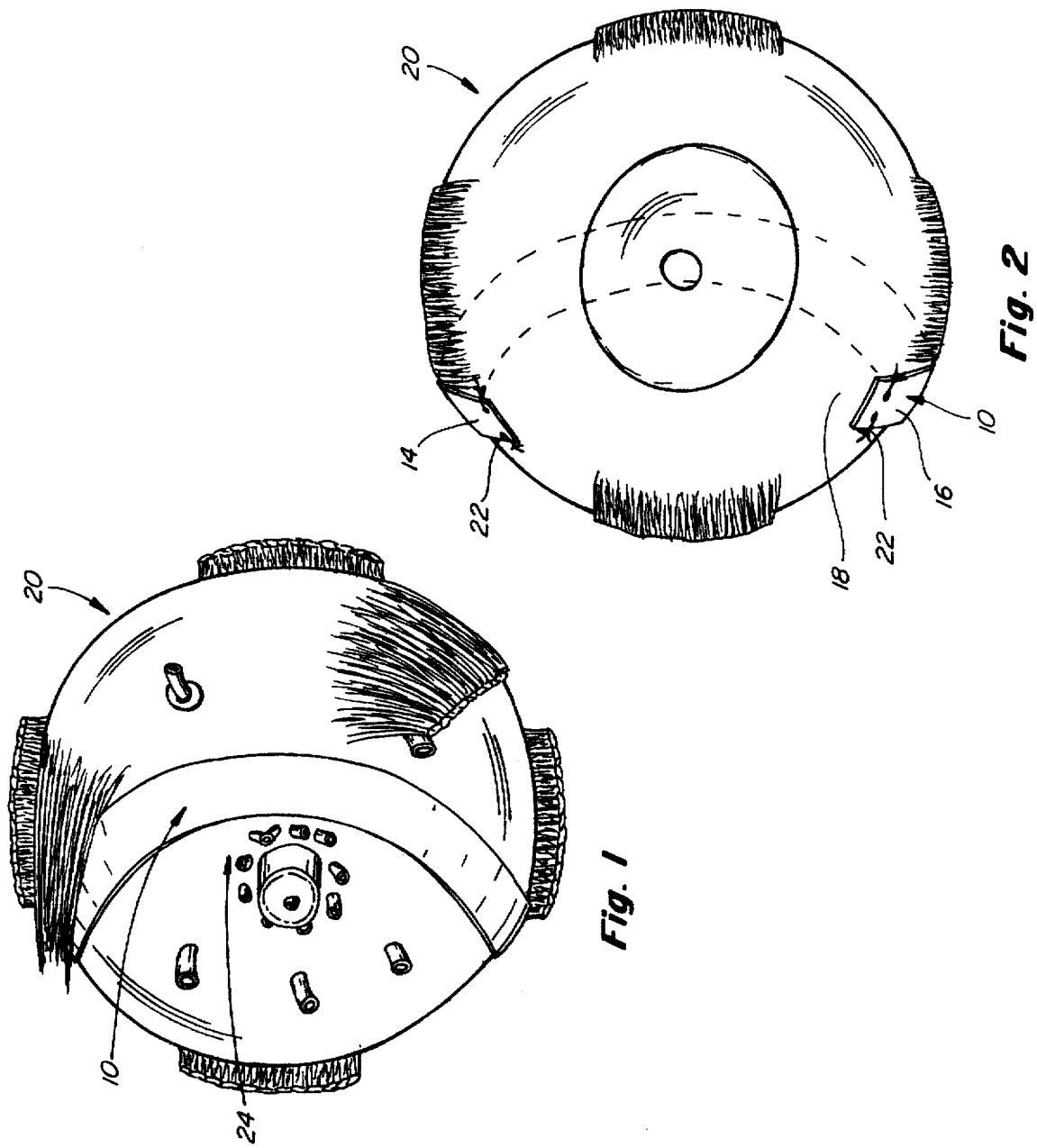

MACULAR BANDAGE FOR USE IN THE TREATMENT OF SUBRETINAL NEOVASCULAR MEMBERS

BACKGROUND OF THE INVENTION

This invention relates to a macular bandage for use in the treatment of subretinal neovascular membranes, and in particular to a macular bandage which is used to reduce vascular congestion in the treatment of subretinal neovascular membranes.

Age-related macular degeneration (AMD) is the leading cause of visual loss among adults aged 65 years or older in Western countries. Although neovascular AMD accounts for only 10% of all cases, it is responsible for 80% to 90% of legal blindness due to this disease and is the most common cause of choroidal neovascularization (CNV) in this age population. The pathological changes leading to CNV involve the complex of tissues in the choriocapilaris, Bruch's membrane, and the retinal pigment epithelium (RPE) with secondary involvement of the neurosensory retina. Essentially anything that alters the retinal pigment epithelium and Bruch's membrane can cause CNV. A variety of conditions other than AMD have been associated with CNV, including ocular histoplasmosis syndrome (POHS), pathologic myopia, angioid streaks, and idiopathic causes. Most histopathological studies have been performed in eyes with AMD. The histopathological feature common to many eyes that develop CNV is a break in Bruch's membrane. The capillary-like neovascularization originates from choroidal vessels and extends through these breaks. Age-related macular degeneration accounts for the largest group of patients with CNV. Most symptomatic CNV's are subfoveal and demonstrate an extremely poor natural history. Subfoveal neovascularization is defined as lesions lying under the geometric center of the foveal avascular zone (FAZ). Of untreated eyes followed for 2 years in a Macular Photocoagulation Study (MPS), only 5% had a final visual acuity better than 20/100, whereas 88% had a final visual acuity of 20/200 or worse. Laser photocoagulation has been the mainstay of therapy for choroidal neovascularization. Through a series of well-executed randomized, prospective clinical trials, the MPS established the superiority of photocoagulation over observation for CNV in a variety of settings. Specifically, photocoagulation treatment of extrafoveal and juxtafoveal neovascular membranes in AMD and other disorders was found to be beneficial compared to the no treatment group. In order to treat the entire area of CNV, the ophthalmologist has to be able to identify the boundaries of the choroidal neovascular membrane. Therefore, treatment is indicated only when the boundaries of the CNV are well demarcated. Unfortunately, occult or ill-defined new vessels are the most common pattern at presentation for exudative macular lesions in AMD. In one study, visible or classic neovascular membranes involved only 23% of eyes referred for treatment. The MPS, recently reported results of photocoagulation for subfoveal neovascular lesions in AMD showed benefit of laser treatment, but the difference between the treatment and observation groups was small and was seen only after two and five years. Also, as the laser energy destroys both the retina and subretinal membrane, there was a precipitous drop in visual acuity associated with treatment. These results underline both the poor natural history of the condition and the limitations of photocoagulation as a treatment modality.

Since the majority of CNV lesions associated with AMD are considered ineligible for laser treatment because of obscured boundaries, size and location, other options have been considered for treatment. One of these options is subretinal neovascular membrane removal using vitrectomy techniques. According to a study by Thomas and colleagues, neovascular membranes in AMD can indeed be removed, but the intrinsic growth patterns of the neovascular complexes limit the visual outcome in most eyes and does not appear to offer significant benefit over observation or laser photocoagulation. In this particular study, of 41 operated eyes, only 5% retained good central visual acuity of 20/40 or better, whereas visual acuity in 88% of the operated eyes were 20/200 or worse. Although the results after removal of choroidal neovascular membranes (CNM) associated with idiopathic and postinflamatory lesions are good, those associated with membranes secondary to angiod streaks and high myopia are similar to those seen in AMD. Clinical evidence and laboratory studies suggest that the integrity of the subfoveal retinal pigment epithelium (RPE) and choriocapillaris is one important factor in determining visual prognosis after submacular surgery. Gass has classified subfoveal membranes in patients with POHS by whether the CNM lies under the RPE (type 1) or between the RPE and the neurosensory retina (type 2). In AMD, the choroidal neovascular membrane is intimately associated with the RPE and the pigment epithelial cells are thus removed at the time of surgery in most patients. Laboratory studies demonstrate that persistent areas of bare, subfoveal RPE will lead to secondary atrophy of the choriocapillaris and outer retina. It is unlikely that refinement of surgical instrumentation will lead to further improvement in visual results in these eyes. Subretinal surgery might help in decreasing the size of the central scotoma at 6 months and 1 year, with remaining vision associated with the development of an eccentric fixation locus.

Interferon alpha-2a has been found to have an anti-angiogenesis effect in vitro and in vivo and is used clinically for the treatment of congenital hemangioma lesions. It has been used in the treatment of CNV from exudative AMD with sistemically administered doses of 3.0 to 6.0 million u/m of body surface area every other night for 8 to 12 weeks. The results have been so far disappointing with zero regression of the CNM in fluorescein angiography and a visual acuity less or equal to 20/200 in 10 patients in one series and no improvement of visual acuity with severe sistemic effects in 90% of 20 patients in another series.

Another technique in the treatment of subfoveal CNM which has been proposed by Coscas is the perifoveal and macular scatter photocoagulation. The first treatment modality was considered effective in preservation of visual acuity, but only if baseline acuity was 20/100 or worse, and also for a limited time. In the case of macular scatter photocoagulation, there was no statistical difference in visual acuity between treated and observed eyes.

Other approaches to the treatment of subfoveal choroidal neovascular membranes at an experimental level include vascular targeting with photodynamic occlusion of subretinal vessels, external beam radiotherapy on the macular region, and subretinal endophotocoagulation of choroidal neovascular membranes. Although some of these treatments appear to be promising, they still need further evaluation, testing, and refinement.

The relationship between AMD or chronic systemic hypertension, and disturbances of the choriocapillary bed in AMD has long been a subject of dispute. Histopathological studies have demonstrated consistent changes in the choroidal vascular bed in patients with AMD and it appears that alterations in the choroidal circulation with age are associated with the development of AMD. These changes include sclerosis of the choriocapillaris with thickening of the septa and narrowing of the lumen and replacement of the sinusoidal capillary network by a tubular system. Indeed, a significant association between AMD and systemic hypertension was demonstrated in human patients.

On the basis of the choroidal anatomy and pathophysiological abnormalities that involve the RPE. Bruch's membrane, and choriocapillaries in AMD, it is speculated that these elements become compromised by excessive permeability of the choroidal vessels. This hyperpermeability of the choroidal vessels leads to the formation of abnormal new vessels which pass through a break in Bruch's membrane to invade the subpigment epithelium and subsensory retinal space. By applying external pressure using a posterior bandage from the scleral side, the bandage attempts to decrease choroidal congestion under the macula and reduces vascular leakage thus preventing abnormal vessel proliferation. This procedure will not reverse the degenerative process of the RPE or destroy the neovascular membrane directly, but it is an attempt to stop or reduce the vascular leakage or hemorrhage that will ultimately lead to destruction of the photoreceptors.

As described above, one of the major limiting factors in successful treatment of subretinal neovascular membranes is the inability to reduce or decrease blood flow through the subretinal neovascular membrane. Thus, a device or treatment method which will reduce vascular congestion or decrease blood flow through the subretinal neovascular member would be advantageous. The present invention is therefore based upon the need and great interest to develop methods and constructions which obviate the limitations of currently available modes of therapies. An ideal device would be one in which bleeding could be reduced or neurosensory fluid accumulation could be reduced in the subretinal neovascular membrane. Additionally, combining a mechanical decongestion device with a local active agent that can stop vascular proliferation provides the best of both worlds.

SUMMARY OF THE INVENTION

A method of treating a disorder of an eye, the eye having a macular area and a sclera, comprises the steps of placing a strip of material over the macular area, the strip having a pair of opposed ends, and suturing the ends to the sclera.

A macular bandage for treating an intraocular structural disorder of an eye, the eye having a macular area and a sclera, the bandage comprises a strip of material having a pair of ends with the strip being placed over the macular area and the ends of the strip being sutured to the sclera with the strip in place to provide buckling in the macular area.

Accordingly, it is an object of the present invention to provide a method of treating a disorder of an eye by providing a macular bandage.

It is another object of the present invention to provide a method of treating a disorder of the eye which does not impair or damage ocular structures.

It is a further object of the present invention to provide a method of treating a disorder of the eye by providing a macular bandage which is used to decrease congestion of the choroid and to decrease blood flow through the subretinal neovascular membrane to decrease bleeding and subretinal fluid accumulation.

A still further object of the present invention is to provide a macular bandage to reduce vascular congestion and to treat subretinal neovascular membranes.

Another object of the present invention is to provide a macular bandage having a therapeutic agent incorporated in the bandage to reduce vascular congestion and to treat subretinal neovascular membranes.

It is an object of the present invention to provide a macular bandage having a circular area centrally positioned on the bandage to reduce vascular congestion and to treat subretinal neovascular membranes.

These and other objects and advantages of the present invention will become apparent after considering the following detailed specification in conjunction with the accompanying drawings, wherein:

BRIEF DESCRIPTION OF THE DRAWINGS

FIG. 1 is a perspective view of a macular bandage constructed according to the present invention placed over an eye as shown from the back of the eye;

FIG. 2 is a partial perspective view of the macular bandage shown in FIG. 1 shown from the front of the eye and shown partially in phantom;

DETAILED DESCRIPTION OF THE PREFERRED EMBODIMENT

Figure 3:
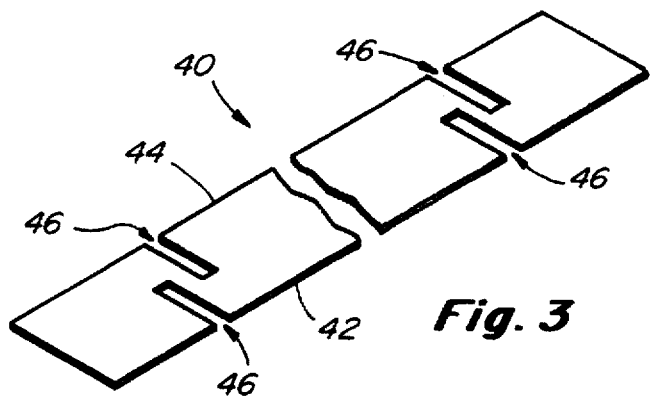
FIG. 3 is a perspective partially broken view of another preferred embodiment of a macular bandage constructed according to the present invention.

Referring now to the drawings, wherein like numerals refer to like items, number 10 identifies a preferred embodiment of the macular bandage which is constructed according to the present invention. With reference now to FIGS. 1 and 2, the macular bandage 10 comprises a strip of material 12 having a pair of ends, such as opposed ends 14 and 16. The strip 12 is made of a suitable non-toxic material such as polytetrafluoroethylene which is also know as Gore-Tex®. The material may also be synthetic material, organic material, or a combination of synthetic and organic materials. For example, silicone may be used and silicone in combination with other synthetic material may be used for the material. Other examples of synthetic materials are nylon and dacron. Examples of organic materials are duramater, fascia lata, or sclera. The strip 12 is shown having the ends 14 and 16 sutured to a sclera 18 of an eye 20. The ends 14 and 16 are sutured to the sclera 18 by 5-0 mersilene suture 22. The strip 12 has any suitable width and length which is dependent upon the size of the eye 20 to be treated. For example, the width of the bandage 10 may vary in the range of 1 to 5 mm and the length of the bandage 10 may vary in the range of 50 to 100 mm. The bandage 10 is used to support or buckle a macular area 24 of the eye 20. Additionally, the bandage 10 may be incorporated with a therapeutic agent for treatment purposes.

The surgical technique or procedure used for applying the macular bandage 10 involves placing the strip 12 over the macular area 24 around the eye 20 and suturing the ends 14 and 16 of the strip 12 to the sclera 18. In particular, a 360 degree limbal peritomy is performed and the four rectus muscles are isolated. The inferior oblique muscle is also isolated. A 6-0 vicryl suture is passed in a locking bite 1 mm away from the insertion and the muscle is disinserted. The strip 12 is then passed under the inferior oblique muscle and the inferior rectus muscle with one end 14 of the strip 12 placed nasal to the inferior rectus muscle. The other end 16 of the strip 12 is passed under the superior rectus muscle for the strip 12 to arc around the eye 20 in a sagittal plane indent the sclera posterior to the macula. The end 16 is brought nasal to the superior rectus muscle. The position of the bandage 10 may be checked by using a fiberoptic light pipe and indirect ophthalmoscope. Once it is verified that the bandage 10 is in a proper position, the ends 14 and 16 are sutured to the sclera 18 in a mattress fashion by using a 5-0 mersilene suture. The lateral rectus muscle is then resutured to its original position. In this manner the bandage 10 is used to decrease the blood flow through the subretinal neovascular membrane to decrease any bleeding and neurosensory fluid accumulation that further decreases vision. The bandage 10 is also left in place sutured to the sclera permanently. Additionally, postoperative examinations may be performed by taking fundus photographs with fluorescein angiograms and indocyanine green (ICG) for the purpose of studying choroidal circulation. Parameters for surgical results include the evaluation of final visual acuity, appearance of the growth of the neovascularization, and secondary complications such as bleeding or exudates.

Patients who may be suitable for a macular bandage may be selected using the following eligibility criteria: (1) preoperative best corrected Snellen visual acuity of 20/400 or better (2.0 according to the modified Bailey-Lovie chart), as determined by manifest refraction by an independent observer; (2) absence of other eye disease that could significantly limit visual acuity; (3) clinical evidence of a subfoveal or juxtafoveal CNM, including the presence of a neurosensory retinal detachment, intraretinal lipid and/or hemorrhage, and/or presence of a green or gray subretinal elevation consistent with a neovascular membrane; (4) angiographic evidence of a subfoveal or juxtafoveal CNM on fluorescein angiography performed no more than 72 hours prior to surgery, and showing ill-defined or occult characteristics, or being too large in size to be amenable to photocoagulation according to the MPS parameters; and (5) patients denying the alternatives of laser photocoagulation or observation.

Figure 4:
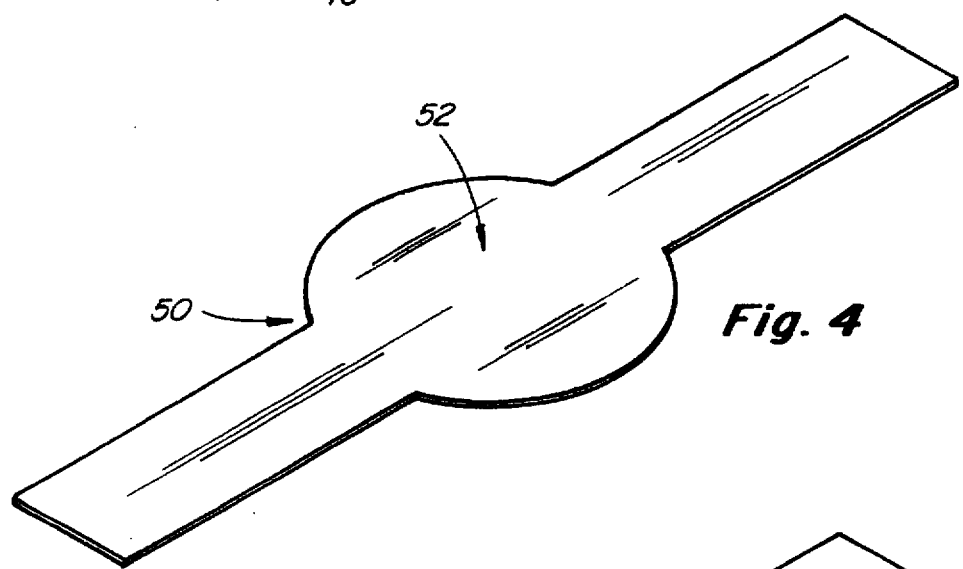
FIG. 4 is a perspective view of a further preferred embodiment of a macular bandage constructed according to the present invention.
Figure 5:
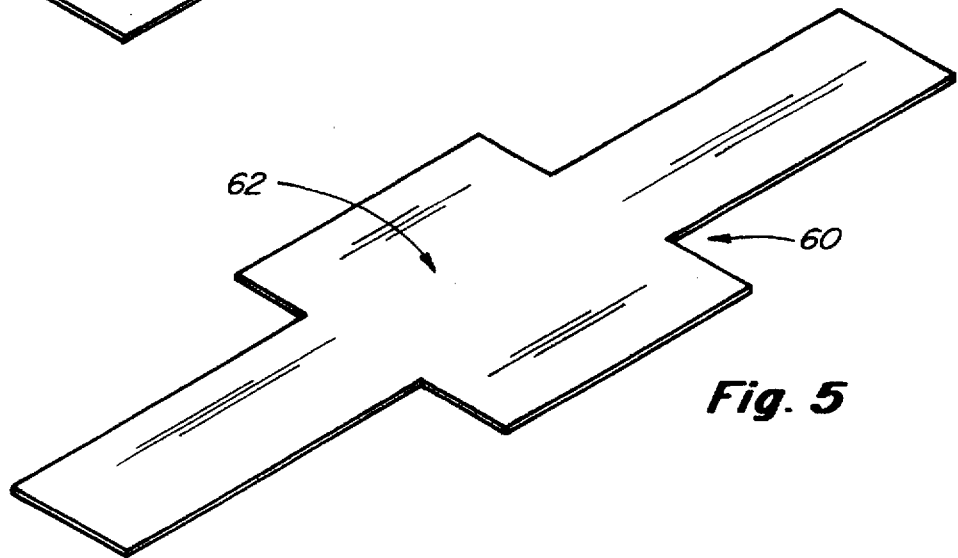
FIG. 5 is a perspective view of another preferred embodiment of a macular bandage constructed according to the present invention.

Additionally, the shape of the bandage 10 may be modified depending upon whether more or less pressure is required on the eye 20. With reference now to FIG. 3, a bandage 40 is shown which has edges 42 and 44 which have cuts 46 made along the edges 42 and 44 which are used to relax the bandage 40. For example, if the intraocular pressure of the eye 20 rises the cuts 46 are made in the bandage 40 to stretch the bandage 40. Additional cuts 46 may be made along the edges 42 and 44 as the case may require. FIG. 4 illustrates another bandage 50 wherein there is a circular area 52 centrally located or positioned on the bandage 50. The circular area 50 is used to further support or apply pressure to the macular area 24 of the eye 20. Although a circular area 52 is shown, other shapes may be made on the bandage 50 to further support or apply pressure to the macular area 24 of the eye 20. Another bandage 60 is depicted in FIG. 5 wherein the bandage 60 includes a drug delivery area 62 which has a drug incorporated therein and the drug delivery area 62 is either incorporated into the bandage 60 or attached to the bandage 60. The drug delivery area 62 may be located anywhere along the length of the bandage 60 and is shown in the center of the bandage 60. Some examples of the drug which may be incorporated in the drug delivery area 62 are therapeutic agents such as 5-FU or daunomycian.

From all that has been said, it will be clear that there has thus been shown and described herein a macular bandage and method of using the macular bandage which fulfills the various objects and advantages sought therefor. It will be apparent to those skilled in the art, however, that many changes, modifications, variations, and other uses and applications of the subject macular bandage and method of using the macular bandage are possible and contemplated. All changes, modifications, variations, and other uses and applications which do not depart from the spirit and scope of the invention are deemed to be covered by the invention, which is limited only by the claims which follow.

What is claimed is:

1. A method of treating a disorder of an eye, the eye having a macular area and a sclera, the method comprising the steps of placing a strip of material over the macular area, the strip having edges and a pair of opposed ends, determining whether placement of the strip has increased intraocular pressure and if so cutting one of the edges to reduce intraocular pressure, and suturing the ends to the sclera.

2. The method of claim 1 further comprising the step of performing a 360 degree limbal peritomy prior to the placing step.

3. The method of claim 1 wherein the strip of material has a width in the range of 1 mm to 5 mm wide and a length in the range of 50 mm to 100 mm.

4. The method of claim 1 wherein the strip of material has an area centrally located on the strip for applying pressure to the macular area.

5. The method of claim 1 further comprising the step of determining whether cutting one of the edges to reduce intraocular pressure has reduced intraocular pressure enough and if not cutting another edge to further reduce intraocular pressure.

6. The method of claim 1 wherein the strip of material is incorporated with a therapeutic agent.

7. The method of claim 1 wherein the strip of material is a strip of polytetrafluoroethylene.

8. The method of claim 1 further comprising the step of isolating the rectus muscles prior to the placing step.

9. The method of claim 1 further comprising the step of determining whether the strip of material has been placed in a proper position after the suturing step.

10. The method of claim 9 wherein the determining step comprises using a fiberoptic light pipe and indirect ophthalmoscope.

11. A method of treating age-related macular degeneration of an eye, the eye having a macular area, rectus muscles, and a sclera, the method comprising the steps of isolating the rectus muscles, passing a strip of material under the rectus muscles, the strip of material having edges, determining whether passing the strip of material under the rectus muscles has increased intraocular pressure and if so cutting one of the edges to reduce intraocular pressure, and suturing the strip of material to the sclera.

12. The method of claim 11 wherein the strip of material is a strip of polytetrafluoroethylene.

13. The method of claim 11 wherein the strip of material is incorporated with a therapeutic agent.

14. The method of claim 11 wherein the strip of material has an area centrally located on the strip for applying pressure to the macular area.

* * * * *